United States Patent
Roessl et al.

(10) Patent No.: US 9,597,050 B2
(45) Date of Patent: Mar. 21, 2017

(54) MULTI-DIRECTIONAL PHASE CONTRAST X-RAY IMAGING

(71) Applicant: KONINKLIJKE PHILIPS N.V., Eindhoven (NL)

(72) Inventors: Ewald Roessl, Henstedt-Ulzburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 111 days.

(21) Appl. No.: 14/373,969

(22) PCT Filed: Jan. 22, 2013

(86) PCT No.: PCT/IB2013/050542
§ 371 (c)(1),
(2) Date: Jul. 23, 2014

(87) PCT Pub. No.: WO2013/111050
PCT Pub. Date: Aug. 1, 2013

(65) Prior Publication Data
US 2015/0036795 A1 Feb. 5, 2015

Related U.S. Application Data

(60) Provisional application No. 61/589,934, filed on Jan. 24, 2012.

(51) Int. Cl.
*A61B 6/00* (2006.01)
*G21K 1/02* (2006.01)
*A61B 6/06* (2006.01)

(52) U.S. Cl.
CPC ............... *A61B 6/484* (2013.01); *A61B 6/06* (2013.01); *A61B 6/4035* (2013.01);
(Continued)

(58) Field of Classification Search
CPC ....... A61B 6/06; A61B 6/4035; A61B 6/4233; A61B 6/484; A61B 6/502; G21K 1/02; G21K 2207/005
(Continued)

(56) References Cited

U.S. PATENT DOCUMENTS 7,245,694 B2 * 7/2007 Jing ...................... A61B 6/025
378/37
7,433,444 B2 * 10/2008 Baumann ............... A61B 6/032
378/145
(Continued)

FOREIGN PATENT DOCUMENTS

EP 1731099 12/2006
JP WO2011/096584 A1 * 8/2011 ............. A61B 6/484
(Continued)

OTHER PUBLICATIONS

T.H. Jensen, et al., "Directional X-Ray Dark-Field Imaging of Strongly Ordered Systems", Physical Review B 82, (2010), pp. 214103-1 to 214103-8.

*Primary Examiner* — Allen C. Ho

(57) ABSTRACT

A phase contrast X-ray imaging system of an object includes an X-ray source, an X-ray detector arrangement, and a grating arrangement with a phase-grating structure and an analyzer-grating structure. The X-ray detector arrangement includes at least eight line-detector units parallel to each other in a first direction, the line-detector units extending linearly in a direction perpendicular to the first direction. The phase-grating structure has a number of linear phase-gratings having a first part with first phase-gratings with slits in the first direction, and a second part with second phase-gratings with slits in a second direction different than the first direction. The analyzer-grating structure has a number of linear analyzer-gratings having a first part with first analyzer-gratings with slits in the first direction, and a
(Continued)

second part with second analyzer-gratings with slits in the second direction.

12 Claims, 13 Drawing Sheets

(52) U.S. Cl.
CPC ............ *A61B 6/4233* (2013.01); *A61B 6/502* (2013.01); *G21K 1/02* (2013.01); *F04C 2270/041* (2013.01); *G21K 2207/005* (2013.01)

(58) Field of Classification Search
USPC .............................................. 378/36, 37, 62
See application file for complete search history.

(56) References Cited

U.S. PATENT DOCUMENTS

| | | | | |
|---|---|---|---|---|
| 7,443,950 B2* | 10/2008 | Sendai | ................. | A61B 6/0414 378/195 |
| 7,486,770 B2* | 2/2009 | Baumann | ............... | A61B 6/032 378/145 |
| 7,492,871 B2* | 2/2009 | Popescu | .................. | A61B 6/00 378/145 |
| 7,522,698 B2* | 4/2009 | Popescu | ................. | A61B 6/032 378/19 |
| 7,522,708 B2* | 4/2009 | Heismann | ................ | A61B 6/00 378/145 |
| 7,532,704 B2* | 5/2009 | Hempel | ................. | A61B 6/032 378/145 |
| 7,535,986 B2* | 5/2009 | Hempel | ............. | A61B 5/02007 378/4 |
| 7,545,907 B2* | 6/2009 | Stewart | .................... | A61B 6/02 378/108 |
| 7,564,941 B2* | 7/2009 | Baumann | ............... | A61B 6/484 378/146 |
| 7,566,172 B2* | 7/2009 | Kashiwagi | ............... | A61B 6/06 378/155 |
| 7,639,786 B2* | 12/2009 | Baumann | ............... | A61B 6/484 378/145 |
| 7,646,843 B2* | 1/2010 | Popescu | ................. | A61B 6/032 356/521 |
| 7,746,975 B2* | 6/2010 | Kashiwagi | ............. | A61B 6/502 378/37 |
| 7,746,981 B2* | 6/2010 | Takahashi | ............. | G01T 1/2928 250/370.11 |
| 7,817,773 B2* | 10/2010 | Stanton | .................. | A61B 6/466 378/15 |
| 7,817,777 B2* | 10/2010 | Baumann | ............... | A61B 6/00 378/36 |
| 7,889,838 B2* | 2/2011 | David | .................. | A61B 6/4233 378/36 |
| 7,924,973 B2* | 4/2011 | Kottler | ................. | G01B 15/025 378/36 |
| 7,945,018 B2* | 5/2011 | Heismann | ............... | A61B 6/032 378/145 |
| 7,949,095 B2* | 5/2011 | Ning | ...................... | A61B 6/032 378/4 |
| 7,983,381 B2* | 7/2011 | David | ................... | A61B 6/032 378/4 |
| 8,005,185 B2* | 8/2011 | Popescu | ................. | A61B 6/06 378/19 |
| 8,009,796 B2* | 8/2011 | Popescu | ................. | A61B 6/032 378/19 |
| 8,009,797 B2* | 8/2011 | Ouchi | .................... | G01N 23/04 378/36 |
| 8,041,004 B2* | 10/2011 | David | .................... | A61B 6/484 378/36 |
| 8,073,099 B2* | 12/2011 | Niu | .......................... | A61B 6/00 378/36 |
| 8,094,776 B2* | 1/2012 | Takahashi | ............... | A61B 6/025 378/21 |
| 8,139,711 B2* | 3/2012 | Takahashi | ................ | A61B 6/00 356/457 |
| 8,184,771 B2* | 5/2012 | Murakoshi | ........ | G01N 23/20075 378/145 |
| 8,280,000 B2* | 10/2012 | Takahashi | ............... | A61B 6/484 378/62 |
| 8,374,309 B2* | 2/2013 | Donath | .................. | A61B 6/032 378/145 |
| 8,411,816 B2* | 4/2013 | Ohara | .................... | A61B 6/484 378/36 |
| 8,451,975 B2* | 5/2013 | Tada | ..................... | A61B 6/4291 378/207 |
| 8,565,371 B2* | 10/2013 | Bredno | .................. | A61B 6/032 378/9 |
| 8,591,108 B2* | 11/2013 | Tada | ........................ | A61B 6/00 378/207 |
| 8,611,495 B2* | 12/2013 | Maschke | .............. | A61B 6/4014 378/197 |
| 8,632,247 B2* | 1/2014 | Ishii | ......................... | A61B 6/00 378/207 |
| 8,755,487 B2* | 6/2014 | Kaneko | ..................... | A61B 6/06 378/36 |
| 8,767,916 B2* | 7/2014 | Hashimoto | ............. | A61B 6/484 378/62 |
| 8,781,069 B2* | 7/2014 | Murakoshi | ........... | A61B 6/4233 378/36 |
| 8,817,948 B2* | 8/2014 | Kusunoki | ........... | H04N 13/0221 378/37 |
| 8,824,629 B2* | 9/2014 | Ishii | ....................... | G01N 23/04 378/62 |
| 8,848,863 B2* | 9/2014 | Schusser | .................. | G21K 1/06 378/16 |
| 8,855,265 B2* | 10/2014 | Engel | ....................... | A61B 6/00 378/36 |
| 8,903,042 B2* | 12/2014 | Ishii | ..................... | A61B 6/4233 378/207 |
| 8,913,714 B2* | 12/2014 | Michel | ............ | G01N 23/20075 250/370.09 |
| 8,995,613 B2* | 3/2015 | Ouchi | .................. | G01N 23/046 378/62 |
| 9,001,969 B2* | 4/2015 | Murakoshi | ........... | A61B 6/4233 378/70 |
| 9,036,773 B2* | 5/2015 | David | .................. | A61B 6/4035 378/36 |
| 9,066,649 B2* | 6/2015 | Roessl | ...................... | A61B 6/00 |
| 9,084,528 B2* | 7/2015 | Geller | ....................... | A61B 6/00 |
| 9,105,369 B2* | 8/2015 | Koehler | .................... | A61B 6/032 |
| 2012/0189101 A1 | 7/2012 | Kaneko | | |

FOREIGN PATENT DOCUMENTS

| | | |
|---|---|---|
| WO | WO2008006470 | 1/2008 |
| WO | WO2009101569 | 8/2009 |
| WO | WO2011070489 | 6/2011 |
| WO | WO2011105306 | 9/2011 |
| WO | WO2012000694 | 1/2012 |
| WO | WO2012052881 | 4/2012 |
| WO | WO2012052900 | 4/2012 |
| WO | WO2013004574 | 1/2013 |

* cited by examiner

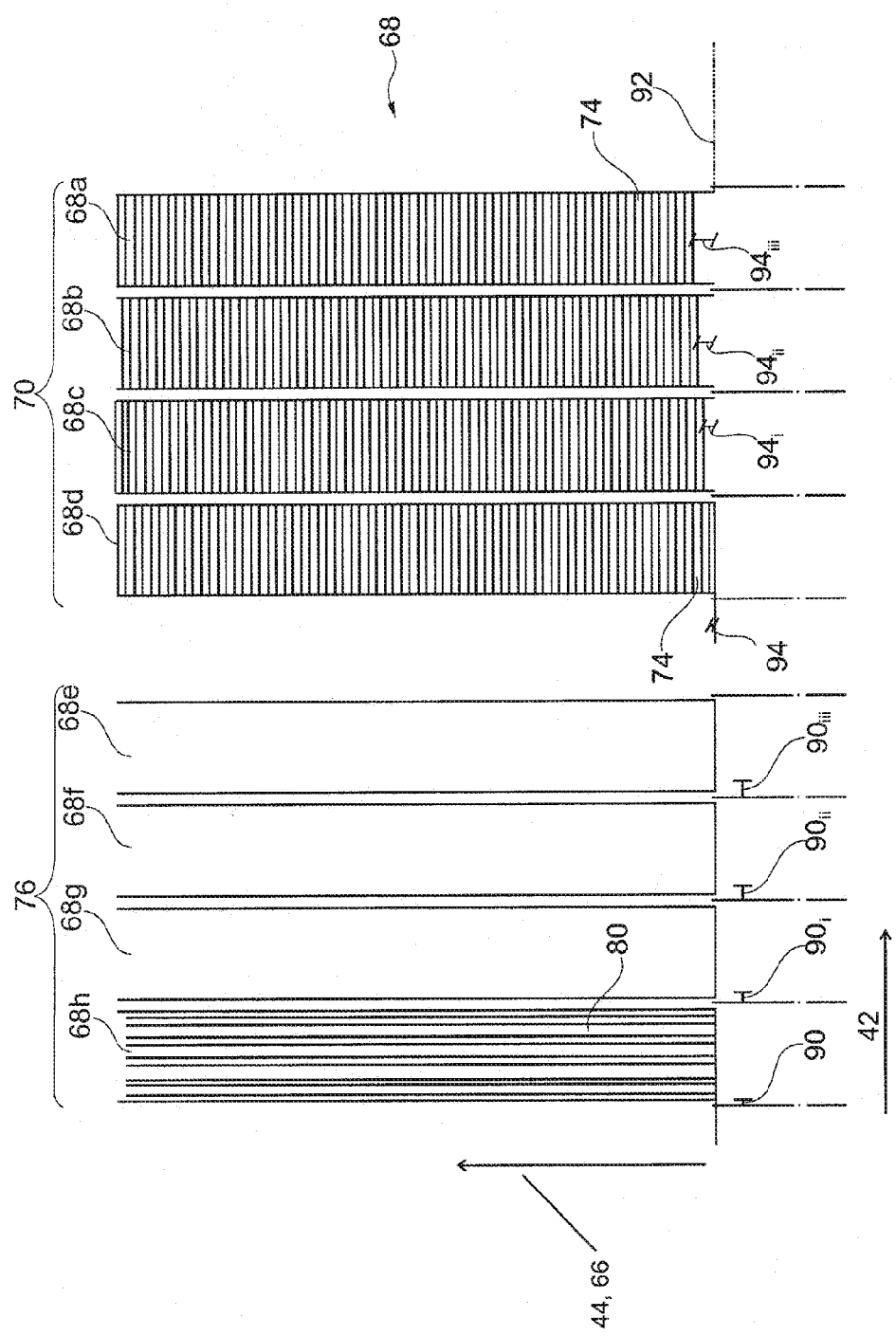

MULTI-DIRECTIONAL PHASE CONTRAST X-RAY IMAGING

CROSS-REFERENCE TO PRIOR APPLICATIONS

This application is the U.S. National Phase application under 35 U.S.C. §371 of International Application Serial No. PCT/IB2013/050542, filed on Jan. 22, 2013, which claims the benefit of U.S. Application Ser. No. 61/589,934, filed on Jan. 24, 2012. These applications are hereby incorporated by reference herein.

FIELD OF THE INVENTION

The present invention relates to an X-ray imaging system for phase contrast imaging of an object, to a method for X-ray phase contrast imaging of an object, and to a computer program element as well as to a computer readable medium.

BACKGROUND OF THE INVENTION

Phase contrast X-ray imaging, i.e. differential phase contrast imaging, is used, for example, to enhance contrast of low-absorbing specimen in comparison to conventional attenuation contrast images. EP 1 731 099 A1, also published as U.S. Pat. No. 7,889,838 B2, describes an X-ray interferometer arrangement comprising a polychromatic X-ray source, a source-grating, a phase-grating, and an analyzer-grating in addition to an image detector. An object is arranged between the source-grating and the phase-grating. The gratings comprise a plurality of X-ray transparent slits between bars of absorbing material, for example gold. However, the X-ray interferometer arrangement is providing phase contrast information in only one direction.

SUMMARY OF THE INVENTION

Thus, there is a need to provide phase contrast information in more than one direction.

The object of the present invention is solved by the subject-matter of the independent claims, wherein further embodiments are incorporated in the dependent claims.

It should be noted that the following described aspects of the invention apply also for the X-ray imaging system, the method for X-ray phase contrast imaging, the computer program element and the computer readable medium.

According to a first aspect of the present invention, an X-ray imaging system for phase contrast imaging of an object is provided that comprises an X-ray source, an X-ray detector arrangement, and a grating arrangement. The X-ray detector arrangement comprises at least eight line-detector units arranged parallel to each other in a first direction, wherein the line-detector units extend linearly in a direction perpendicular to the first direction. The X-ray source, the X-ray detector arrangement and the grating arrangement are adapted to perform an acquisition movement in relation to an object in a scanning direction, wherein the scanning direction is parallel to the first direction. The grating arrangement comprises a phase-grating structure arranged between the X-ray source and the detector, and an analyzer-grating structure arranged between the phase-grating structure and the detector arrangement. The phase-grating structure is having a number of linear phase-gratings, each of which is arranged in fixed association with an assigned line of the at least eight line-detector units. A first part of the phase-gratings is provided as first phase-gratings with slits in the first direction, and a second part of the phase-gratings is provided as second phase-gratings with slits in a second direction different to the first direction. The analyzer-grating structure has a number of linear analyzer-gratings, each of which is arranged in fixed association with an assigned line of the at least eight line-detector units. A first part of the analyzer-gratings is provided as first analyzer-gratings with slits in the first direction, and a second part of the analyzer-gratings is provided as second analyzer-gratings with slits in the second direction. At least four adjacent lines of the line-detector units are associated with the first phase-gratings and the first analyzer-gratings, and at least four adjacent lines of the line-detector units are associated with the second phase-gratings and the second analyzer-gratings.

According to the present invention, the provided X-ray radiation has to show a respective transverse coherency, for example generated with an appropriately adapted source-grating. In other words, the transverse coherence of the X-rays must be large in the direction perpendicular to the scan direction relating to the first grating direction and large in the second direction different to the first direction in relation to the respective area, i.e. parts, of the phase grating with its different grating orientations. For example, in a source-grating, metal bar structures, e.g. metal-filled groove or trench structures, must be oriented parallel to the first direction in one part and parallel to the second direction in the other part. As the coherency of the X-rays in the projected areas of the intermediate regions is poorly defined, the corresponding detector line, or detector lines, may not be covered by gratings, as mentioned in one of the described examples. Of course, instead of providing a source-grating adapted to the at least two coherence directions, also a respective X-ray source providing the respective radiation with multi-coherence can be provided. In case an X-ray source is provided that is capable of applying a respective coherent X-ray radiation, wherein the direction of the coherence of different parts of the X-ray radiation is aligned or adapted to the respective grating structure parts' coherence direction, the source-grating structure can also be omitted. The latter could be achieved by a sufficiently small focal spot.

The gratings of the grating arrangement for providing phase contrast imaging are provided with a plurality of bars and gaps being arranged periodically, wherein the bars are arranged such that they change the phase and/or amplitude of an X-ray radiation and wherein the gaps are X-ray transparent. According to the present invention, the term "X-ray transparent" relates to the fact that X-ray radiation passing the grating is not changed in its phase, i.e. it is not phase-shifted, and not changed in its amplitude, both to a measurable or reasonable amount. According to the present invention, the term "changing phase" relates to shifting the phase of the X-ray radiation. The bars of the analyzer-grating are X-ray absorbing such that they are changing the amplitude of X-ray radiation passing the grating. The bars of the phase-grating are changing the phase of the X-ray radiation passing the grating.

According to an exemplary embodiment of the present invention, the fixed association comprises a variation in a phase-grating to analyzer-grating offset by a fraction 1/n of the pitch of the analyzer-grating; wherein n is the number of lines of the line-detector units associated with one type of phase-grating.

According to an example, in relation with the adjacent lines, the "fixed association" comprises an additional offset, or additional displacement, between the grating pitch of the phase-grating and the analyzer-grating, such that the actual displacement/offset position for the $x^{th}$ analyzer-grating pitch to the phase-grating pitch of the first part or the second part is $d=(x-1)/n$. For example, in case of n=4 detector lines for each phase-grating direction, the grating assigned to the first of the four detector lines is provided with an offset $d=(1-1)/4=0$, the analyzer-grating assigned to the second of the four detector lines is provided with an offset $d=(2-1)/4=\frac{1}{4}$ pitch of the analyzer-grating, the grating assigned to the third of the four detector lines is provided with an offset $d=(3-1)/4=\frac{1}{2}$, and the grating assigned to the fourth of the four detector lines is provided with an offset $d=(4-1)/4=\frac{3}{4}$ pitch of the analyzer-grating. Similar rules apply to the detector lines associated with the gratings in the other direction. The offset can be increasing, or decreasing. Further, it must be noted that the phase grating pitch and the analyzer grating pitch can have a ratio of 2 to 1, i.e. the pitch of the analyzer grating is half the size of the pitch of the phase grating. This is true for parallel geometry. In case of differing cone beam geometries, there is a magnification effect, which relates the pitch of the gratings.

According to a further example, a number of z*n lines of the line-detector units associated with one type of phase-grating is provided, and a redundancy of z is provided; for example, four plus four lines in each direction, each four lines provided with an offset of ¼ providing a redundancy of 2.

According to a further exemplary embodiment, at least twelve line-detector units are provided, wherein a further part of the phase-gratings is provided as further phase-gratings in a further direction and a further part of the analyzer-gratings is provided as further analyzer-gratings in the further direction, each of which is arranged in fixed association with an assigned line of the at least twelve line-detector units. The further direction is different from the first and second direction.

For example, the first direction could be parallel to the scanning direction, the second direction would be arranged in an angle 60° to the first direction and the further direction in an angle of 120°.

According to a further exemplary embodiment, for the acquisition movement, the gratings remain fixed in relation to each other and in relation to the detector arrangement. For example, for the acquisition movement, no phase stepping is provided.

According to a further exemplary embodiment, for the acquisition movement, the X-ray source, the grating arrangement, and the X-ray detector arrangement are mounted to a movement structure that is pivotable around an axis aligned with a focal spot of the X-ray source.

According to a further exemplary embodiment, at least one further line-detector unit is provided as a pure attenuation measuring detector unit without an associated phase and analyzer-grating structure.

According to a further exemplary embodiment, a pre-collimator is provided between the X-ray source and the analyzer-grating such that an object can be arranged between the X-ray source and the analyzer-grating. A post-collimator is provided between the analyzer-grating and the detector.

According to a second aspect of the present invention, a method for X-ray phase contrast imaging of an object is provided, comprising the following steps:
a) acquiring phase contrast image sub-data with a detector having at least eight detector lines, wherein at least four detector lines are relating to a first phase direction of a grating structure and at least further four detector lines are relating to a second phase direction, wherein each line of the line-detector units relating to one phase direction is arranged in fixed association with the grating structure pitch;
b) moving the detector in relation to the object with an acquisition movement in a single direction;
wherein steps a) and b) are repeatedly performed at least eight times such that image information of one point is acquired by each of the detector lines;
c) computing a phase-retrieval, generating image data for each of the detector lines; and
d) providing the image data for further steps.

The fixed association comprises a variation in a phase-grating to analyzer-grating offset by a fraction 1/n of the pitch of the analyzer-grating; wherein n is the number of lines of the line-detector units associated with one type of phase-grating. For the acquisition, X-ray radiation with coherency in at least two directions, i.e. coherency in one direction for the rays passing the first set of detectors and coherency in another direction for the second set of detectors, is provided in accordance with the respective differently oriented grating structures.

According to a further exemplary embodiment, the phase-retrieval in step c) provides: i) differential phase data; ii) scatter information; and iii) attenuation data.

According to an aspect of the present invention, the gratings are provided with at least two different grating directions, thus providing phase contrast image information concerning the respective two different directions. Instead of the usually applied stepping of the gratings in order to scan different portions of the resulting interference pattern, the imaging system is moved in relation to the object to be examined. The number of four line-detector units is provided as a minimum, in order to be able, for example, to identify a sinusoidal curve in the intensities measured for the same physical rays by different detector lines corresponding to different offsets between the respective phase and analyzer gratings. Of course, a higher number of so-to-speak scanning lines, each relating to different portions of the interference pattern, due to the offset from one scanning line to the next scanning line, i.e. the offset increasing or decreasing between the phase-grating and the analyzer-grating, the respective image information is provided that can then be computed in a phase-retrieval step in order to arrive at the desired phase contrast image data.

According to a further aspect of the present invention, the X-ray imaging system is a mammography system, for example Philips MicroDose mammography systems, wherein the entire field of view is scanned with several linear detector units. For example, the detector units are mounted to a moving structure, which is pivotably mounted such that the focal point of the X-ray source is the rotating point. According to the present invention, such mammography system is provided with the grating arrangement according to the present invention, as described above, such that a so-called slit scanning system can acquire phase contrast information without the need for phase stepping in the conventional sense where one of the phase or analyzer gratings in the system has to be physically displaced with respect to the other. For example, making use of the twenty-one detector lines present in the Philips MicroDose system, an equivalent of the phase stepping is implemented in the system where one after the other detector lines provides samples of one and the same physical ray path through the breast. Therefore, the different line-detectors are complemented by gratings interferometers with different frozen phase states.

Two or more phase cycles are acquired with a line-detector system simultaneously by orienting phase-related grating structures at various angles with respect to the scanning direction. In one possible embodiment, the first seven line-detectors are used to acquire phase contrast in a direction parallel to the scan direction, the following seven line-detectors are used to acquire pure attenuation information, and the last seven line-detectors are used to acquire phase contrast information perpendicular to the scan direction. Instead of seven plus seven plus seven, also two groups of ten detector lines for the gradients in two different directions using a larger portion of the total X-ray flux for the phase contrast acquisition can be provided, and only one line, for example the central detector line, is not designed to acquire phase contrast, but to acquire pure attenuation information.

According to a further aspect, the present invention allows solving the symmetry breaking property of one dimensional differential phase contrast imaging, for example by providing two perpendicular scanning directions. In case of three or more, for example four, directions, for example 0°, 45°, 90° and 135° with respect to the scanning direction, improved image information, in particular for low absorbing portions of an object, such as for breast imaging, can be provided. Thus, significantly reducing the symmetry breaking as the gradient in two or more directions can be acquired, the likelihood of missing strong gradients or strongly scattering tissue components is significantly reduced.

These and other aspects of the invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 7 shows an offset between adjacent phase-gratings and analyzer-gratings, respectively.

DETAILED DESCRIPTION OF EMBODIMENTS

Figure 1:
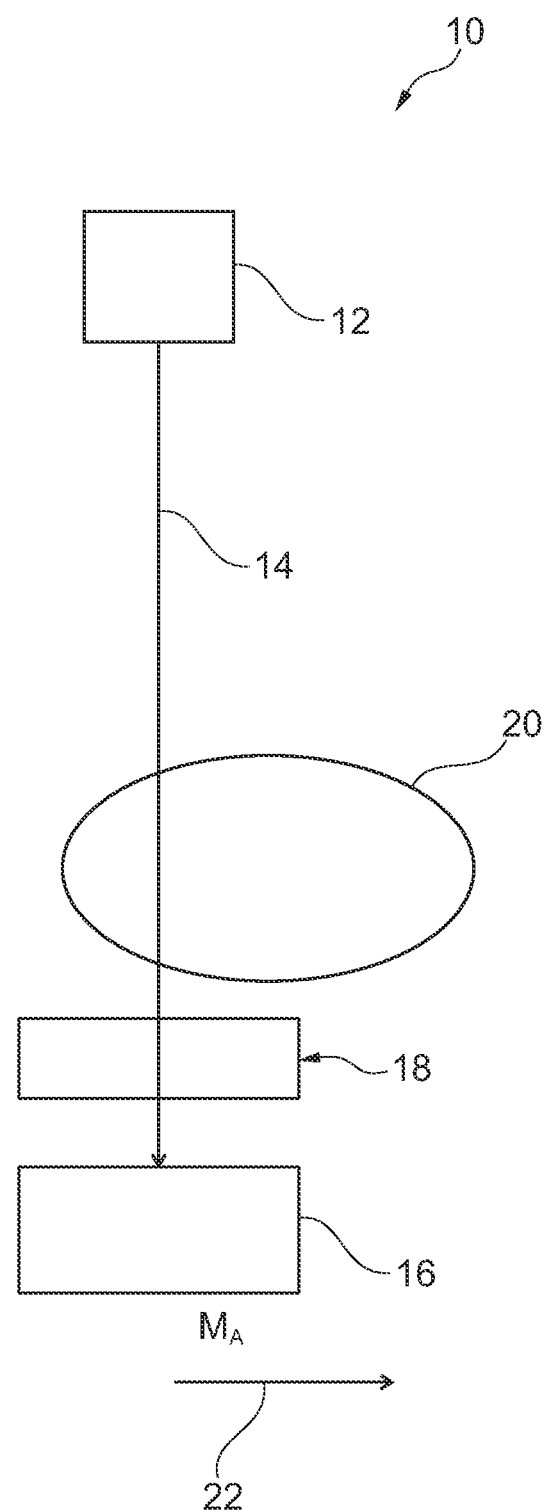
FIG. 1 schematically shows an X-ray imaging system according to an exemplary embodiment of the present invention.

FIG. 1 shows an X-ray imaging system 10 for phase contrast imaging of an object. The X-ray imaging system 10 comprises an X-ray source 12 for radiating X-ray radiation 14 towards an X-ray detector arrangement 16. Further, a grating arrangement 18 is provided, shown in a simplified manner with a box. However, the grating arrangement 18 according to the present invention will be described also with reference to the following figures, in particular FIGS. 3 and 4, and FIGS. 5 to 9.

Further, an object 20 is symbolically indicated. The X-ray source 12, the X-ray detector arrangement 16, and the grating arrangement 18 are adapted to perform an acquisition movement $M_A$ in relation to an object 20 in a scanning direction 22, wherein the scanning direction 22 is also referred to as first direction, i.e. the scanning direction 22 is parallel to the first direction.

Figure 2:
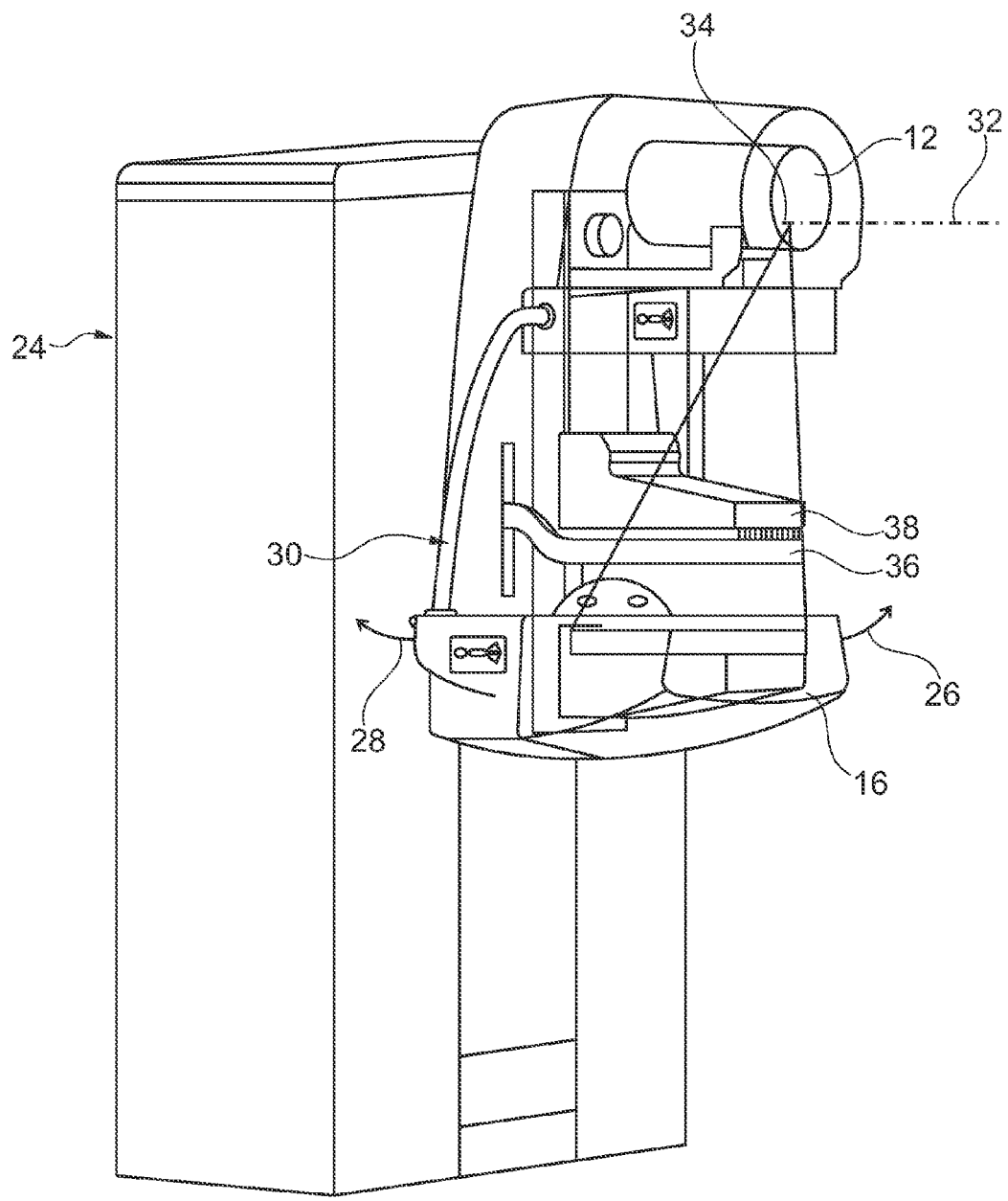
FIG. 2 shows a perspective view of a mammography system as an example for an X-ray imaging system for phase contrast imaging of an object according to the present invention.

Before explaining further the X-ray detector arrangement 16 and the grating arrangement 18 according to the present invention, it is referred to FIG. 2, showing a mammography imaging system 24, in which the scanning direction 22 is indicated with a first arrow 26, and the opposite direction is indicated with a second arrow 28. In the mammography imaging system 24 shown in FIG. 2, the X-ray source 12 and the X-ray detector arrangement 16 are mounted to a movement structure 30 that is pivotable around an axis 32 aligned with a focal spot 34 of the X-ray source 12. Thus, for the acquisition movement $M_A$, the grating arrangement 18 (not further shown in FIG. 2) remains fixed in relation to the X-ray detector arrangement 16. With relation to the mammography investigations, a lower breast support paddle 36 and an upper breast support paddle 38 are provided, which can be displaced in relation to each other in order to receive a breast to be examined as the object 20. For the acquisition, the breast stays in place, and rather the X-ray detector arrangement 16 moves in relation to the breast, together with the X-ray source 12. By providing the axis 32 aligned with the focal spot 34 of the X-ray source 12, a pivoting motion can be implemented. Of course, also other movement types, for example a translational movement of the X-ray source 12 and the X-ray detector arrangement 16 and the grating arrangement 18 can be provided with a different respective mechanism.

Figure 3:
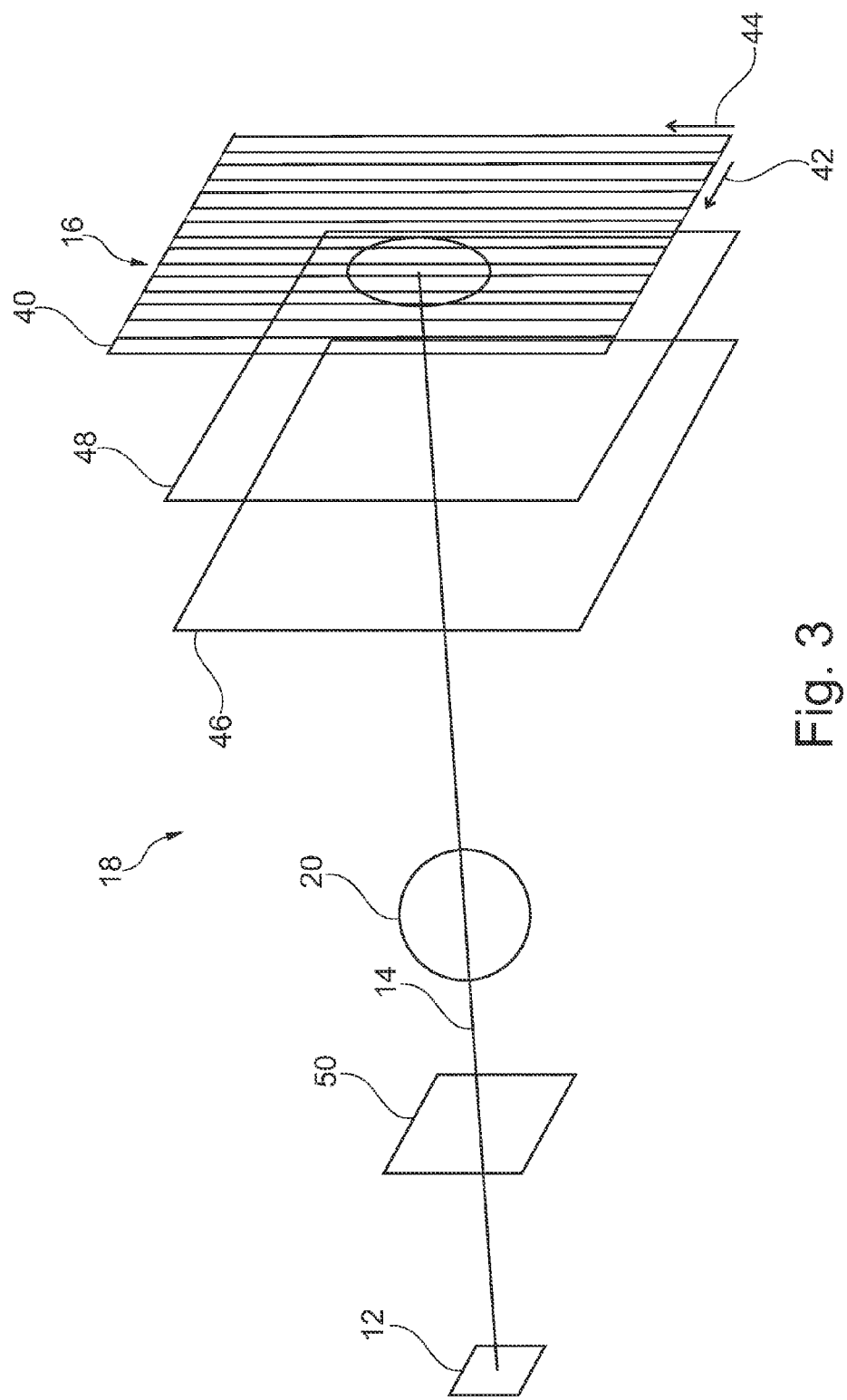
FIG. 3 schematically shows a basic setup for an arrangement of an X-ray imaging system of the present invention.

As shown in FIG. 3, according to the present invention, the X-ray detector arrangement 16 comprises at least eight line-detector units 40 arranged parallel to each other in a first direction, indicated with a first direction arrow 42, wherein the line-detector units 40 extend linearly in a direction, indicated with a second direction arrow 44, perpendicular to the first direction. In other words, the line-detector units 40 are running in the second direction 44, which is perpendicular to the parallel stacking order represented by the first direction 42.

The grating arrangement 18 comprises a phase-grating structure 46 arranged between the X-ray source 12 and the X-ray detector arrangement 16, and an analyzer-grating structure 48 arranged between the phase-grating structure 46 and the X-ray detector arrangement 16.

It must be noted that with respect to FIG. 3, and also with respect to FIG. 1, the arrangement of the different grating structures and the object 20 can be provided in such positioning that starting from the X-ray source 12, the object 20 is provided in front of the phase-grating structure 46, or, according to a further example, arranged following the phase-grating structure 46 and before the analyzer-grating structure 48. Thus, although not shown in FIG. 3, the object 20 could also be arranged between the phase-grating structure 46 and the analyzer-grating structure 48 (see also FIG. 4).

Further, the grating arrangement 18 may comprise a source-grating structure 50 arranged between the X-ray source 12 and the phase-grating structure 46. The source-grating structure 50 is also further explained with relation to FIG. 10 below. The source-grating structure 50 is adapted to provide sufficient coherence to the X-ray beam passing the source-grating structure 50, so that after passing the phase-grating structure 46, the interference can be observed at the location of the analyzer-grating structure 48. The source-grating structure 50 has a number of linear source-gratings, wherein a first part of the source-gratings is provided as first source-gratings providing coherence with relation to the first direction 42, and at least a second part of the source-gratings is provided as second source-gratings providing coherence with relation to the second direction 44. It must be noted that the X-ray radiation 14 has to be provided with at least two coherence directions, which will be explained below in relation with FIG. 5 et seq. This can be provided, according to a first example, by the source-grating structure 50 towards which polychromatic X-ray radiation is radiated and the source-grating structure 50 provides the necessary coherence. Of course, the necessary coherence can also be provided by the X-ray source 12 itself such that the source-grating structure 50 can also be omitted, according to a further example (not further shown).

The source-grating structure 50 has a number of linear source-gratings, wherein a first part is providing coherence with relation to the first direction 42, and at least a second part is providing coherence with relation to the second direction 44.

For example, the source-grating, or source-grating structure 50, is arranged close to the focal spot 34 of the X-ray source 12.

Figure 4:
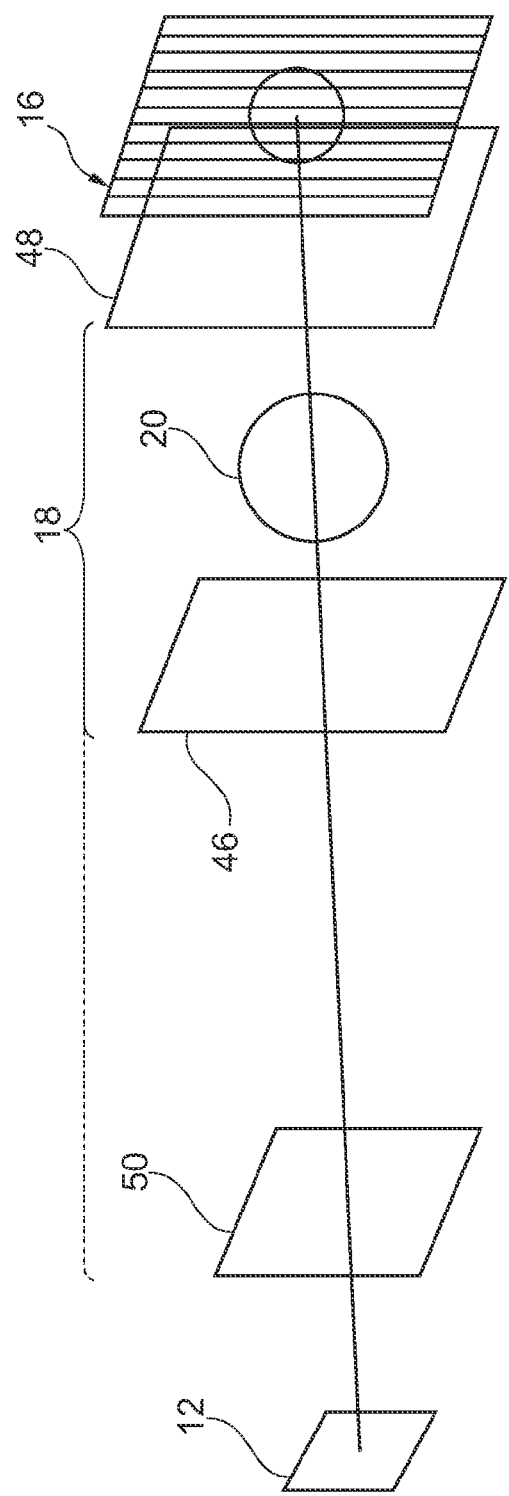
FIG. 4 shows a further possible arrangement in addition to FIG. 3.

FIG. 4 shows a schematic setup, as mentioned above, where the object 20 is arranged between the phase-grating structure 46 and the analyzer-grating structure 48.

Figure 5:
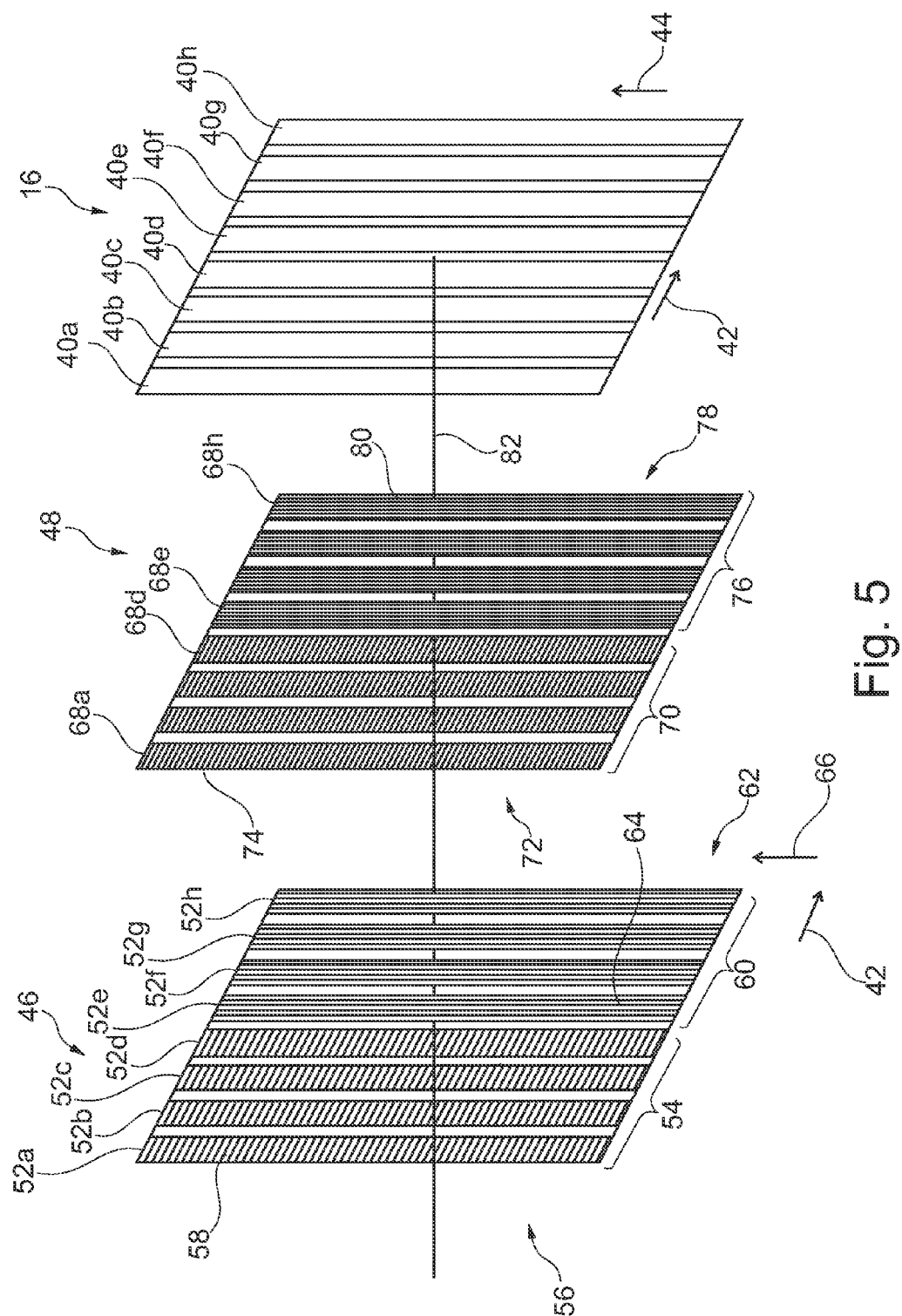
FIG. 5 shows a perspective view of a grating arrangement and an X-ray detector arrangement according to an exemplary embodiment of the present invention.

As shown in FIG. 5, the phase-grating structure 46 has a number of linear phase-gratings 52, each of which is arranged in fixed association with an assigned line of the at least eight line-detector units 40.

The example shows eight lines, indicated with index a to h, in addition to the reference numeral 40, i.e. lines $40_a$ to $40_h$. Similar numbering has been applied to the phase-gratings $52_a$ to $52_h$. A first part 54 of the phase-gratings 52, namely the phase-gratings $52_a$, $52_b$, $52_c$, and $52_d$, is provided as first phase-gratings 56 with slits 58 in the first direction 42. A second part 60 of the phase-gratings 52, namely $52_e$, $52_f$, $52_g$, and $52_h$, is provided as second phase-gratings 62 with slits 64 in a second direction 66 different to the first direction 42. The second direction 66 may be provided parallel to the second or extension direction 44.

The analyzer-grating structure 48 is provided in a similar way, although with a pitch of the respective gratings which is half the size of the pitch of the phase-grating structure 46 in the case of parallel beam geometry. Theoretically, other relations between the phase pitch and the analyzer pitch may be provided depending on the divergence of the beam. Since the respective grating structure principles in differential phase contrast X-ray imaging are known to a skilled person, the relation between the pitch and the distance of the gratings and the detector are also not further discussed at this point.

With reference to FIG. 5, the analyzer-grating structure 48 is having a number of linear analyzer-gratings 68, for example in case of eight line-detectors as eight linear analyzer-gratings $68_a$ to $68_h$. Each of the analyzer-gratings 68 is arranged in fixed association with an assigned line of the at least eight line-detector units 40. A first part 70 of the analyzer-gratings 68 is provided as first analyzer-gratings 72 with slits 74 in the first direction 42. A second part 76 of the analyzer-gratings 68 is provided as second analyzer-gratings 78 with slits 80 in the second direction 66. Thus, the first part 70 comprises the analyzer-gratings $68_a$ to $68_d$, and the second part 76 comprises the analyzer-gratings $68_e$ to $68_h$.

As can be seen from FIG. 5, the respective first and second parts of the phase-grating structure 46 and the analyzer-grating structure 48 are arranged with an aligned orientation of the respective grating structures with regard to the overlapping arrangement in a successive arrangement of the radiation path, indicated with central radiation line 82.

At least four adjacent lines of the line-detector units 40 are associated with the first phase-gratings 56, for example the lines $40_a$ to $40_d$ associated with the phase-gratings $52_a$ to $52_d$. The four adjacent lines of the line-detector units 40 are also associated with the first analyzer-gratings 72, for example the analyzer-gratings $68_a$ to $68_d$. Further, at least four adjacent lines of the line-detector units 40 are associated with the second phase-gratings 62 and the second analyzer-gratings 78. For example, the lines $40_e$ to $40_h$ are associated with the phase-gratings $52_e$ to $52_h$, and the analyzer-gratings $68_e$ to $68_h$.

Figure 6:
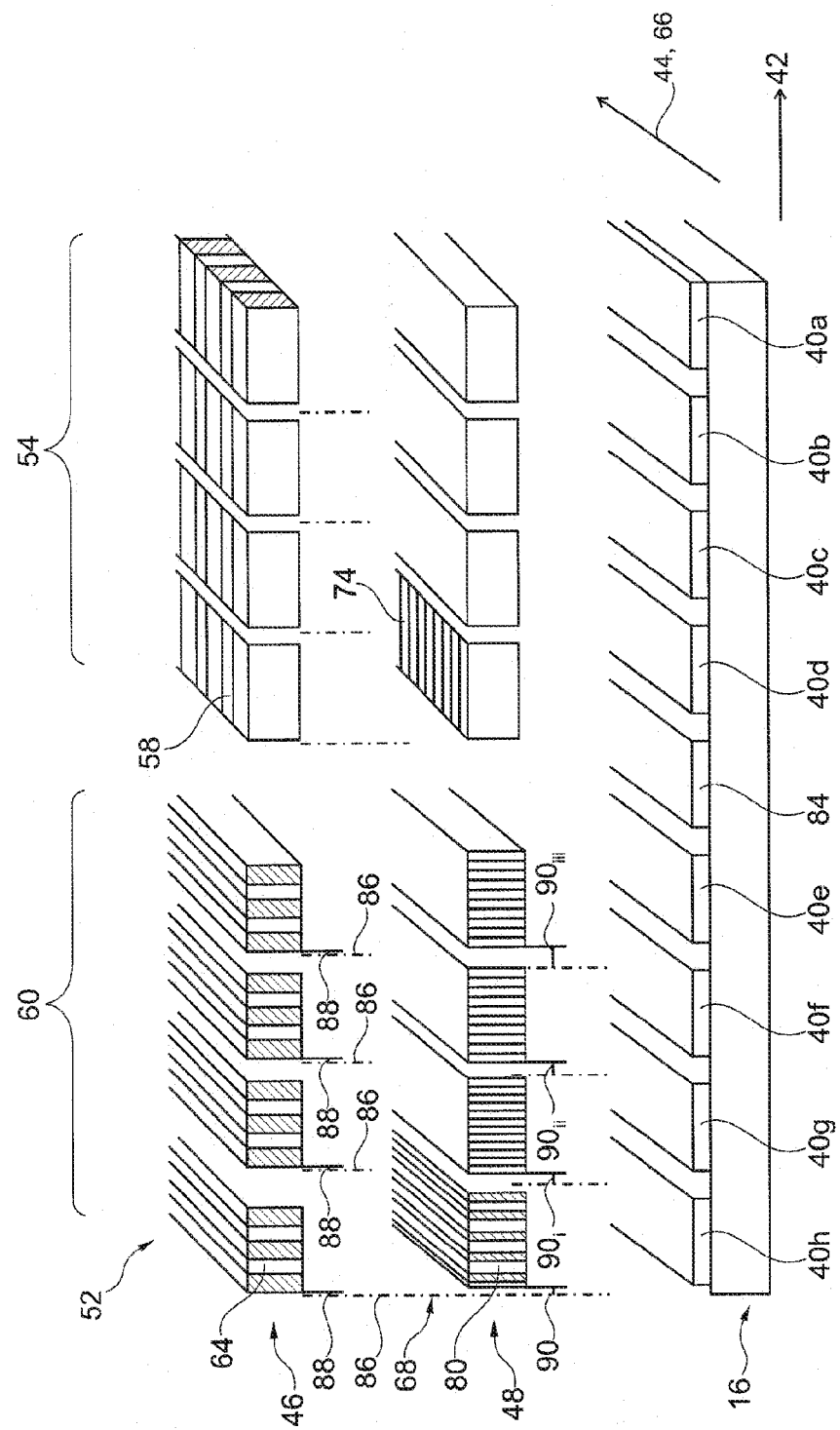
FIG. 6 shows a further perspective view of a further example of a grating arrangement and an X-ray detector arrangement according to the present invention.

The term "fixed association" shall be further explained in relation with FIG. 6, showing a schematic arrangement of the X-ray detector arrangement 16 in the bottom part, on top of which the analyzer-grating structure 48 is shown, followed by the phase-grating structure 46. Of course, the drawing is not to scale and does not show any particular relations with respect to distance or aspect ratio. The X-ray detector arrangement 16 is shown with nine line-detector units 40. It must be noted that the arrangement and order of the respective lines $40_a$ to $40_h$ is shown in a rotated orientation compared to the previous figures, i.e. starting with a on the right side and ending with h on the left side, thus having the first gratings 56, 72 also on the right half and the second gratings 62, 78 on the left half.

In addition to the above-described eight detector lines $40_a$ to $40_h$, a further line-detector unit 84 is provided as a pure attenuation measuring detector unit without any associated phase and analyzer-grating structures. It must be noted that with respect to the aspect of the offset described in the following, the further line-detector unit 84 can also be omitted, or be replaced by a larger number of attenuation measuring line-detector units.

The phase-gratings 52 of the phase-grating structure 46 are shown with the slits 58 for the first part 54 running in the first direction 42 and with the slits 64 for a second part 60 running in the second direction 44. Similar is the case of the analyzer-gratings 68 shown also with the slits 74 running parallel to the slits 58 for the first part 70 (not further indicated) and the slits 80 for the second part 76.

Further, the line-detector units 40 are shown with a respective distance to the adjacent line-detector unit, which distance may be provided due to manufacturing aspects of the line-detector units. However, the distance is not a condition and can also be omitted in case the respective detector technology provides a seamless arrangement of line-detector units 40. Similar applies to the shown structure of the gratings, where the gratings are also shown with a distance to each other for an improved readability of the drawings. Of course, the gratings can also be provided abutting each other, or also with a larger distance. The different grating structures can be provided in an integrated grating body structure.

Dash-dotted lines 86 indicate so-to-speak a grating structure axis. For example, the first of the phase-gratings 52, when starting from the left in FIG. 6, have a distance 88 from the grating structure axis 86 to the starting point of the first bar of the respective grating structure. This distance 88 is provided as the same distance for all of the phase-gratings 52. However, with respect to the analyzer-gratings 68, also these are provided with a distance 90 between the grating structure axis 86, or so-to-speak system axis; and the starting of the first bar of the analyzer-grating structure 48. The fixed association comprises a variation in a phase-grating to analyzer-grating offset by a fraction 1/n of the pitch of the analyzer-grating, wherein n is the number of lines of the line-detector units 40 associated with one type of phase-grating. In other words, the distance 90 increases from one analyzer-grating 68 to the next, which is indicated with an index $90_i$, $90_{ii}$ and $90_{iii}$. Since the phase-gratings 52 are provided with the same distance 88, an increasing offset is thus provided with respect to the arrangement of the phase-gratings 52 to the analyzer-gratings 68. Similar also applies to the other part of the gratings, i.e. the first part 54 of the phase-gratings 52 in relation to the first part 70 of the analyzer-gratings 68.

This is shown in FIG. 7, where for illustration purpose only the analyzer-gratings 68 are shown in a planar view in viewing direction of the X-ray radiation 14. As can be seen, the second part 76, in form of the analyzer-gratings $68_e$ to $68_h$, is provided with the respective distance 90. In the right half, the first part 70 in form of the analyzer-gratings $68_a$ to $68_d$ is shown, wherein the starting of the grating structure is shown in relation to a further system axis 92, indicated with a further dash-dotted line. The analyzer-grating $68_d$ starts with the first bar with a distance 94, which distance 94 is provided with a similar offset by a fraction 1/n as the above described distance 90 in relation with the second part 76. Therefore, the same index i to iii is also used.

Figure 8A:
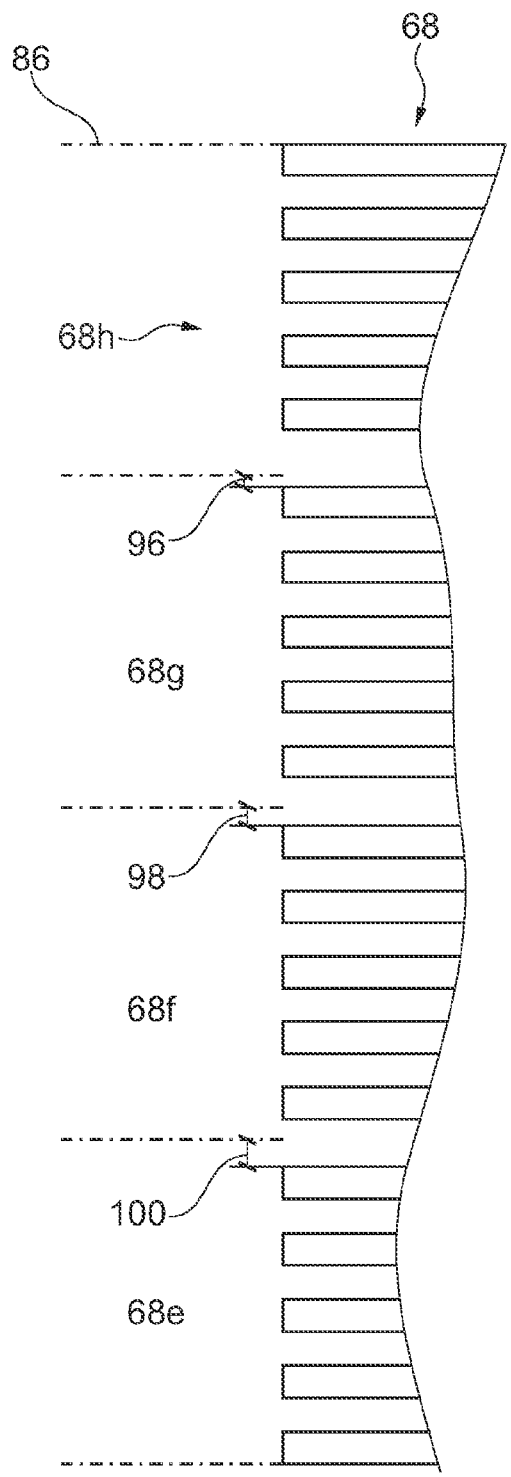
FIGS. 8A and 8B show a more detailed illustration relating to the offset.

This can also be seen from FIG. 8A, showing a further example for the offset of the second part 76 of the analyzer-gratings $68_h$ starting at the top and $68_e$ at the bottom. As can be seen, the upper analyzer-grating starts with the bar structure directly at the system axis 86, wherein the one below is provided with a first offset 96. The one further below, i.e. the analyzer-grating $68_f$ is provided with a further increased offset 98, and the one below that, i.e. analyzer-grating $68_e$ is provided with a still further increased offset 100.

Figure 8B:
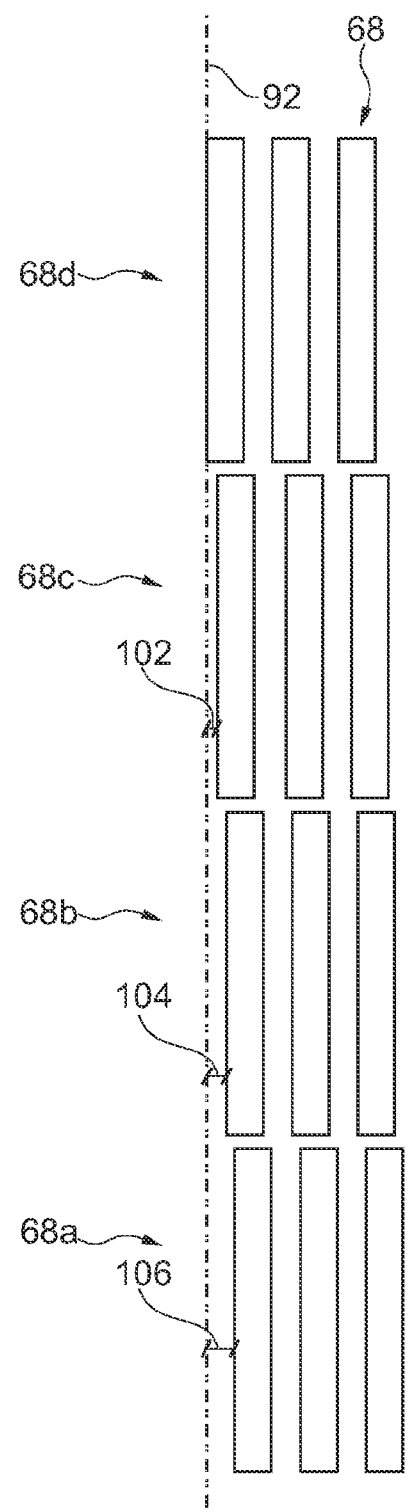

Similar applies to the first part 70 of the analyzer-gratings 68 shown in FIG. 8B, where from top to bottom the analyzer-gratings $68_d$ to $68_a$ are shown. The grating starts at the second system axis 92 at the upper analyzer-grating $68_d$, and the grating of the analyzer-grating $68_c$ below is provided with an offset 102. The next analyzer-grating, i.e. analyzer-grating $68_b$, starts with a further increased offset 104, which is also the case for the below analyzer-grating $68_a$, provided with a still further increased offset 106.

It must be noted in general that according to an alternative example (not shown), all analyzer gratings are aligned to the structure axis and offsets are implemented at the phase gratings.

Figure 9A:
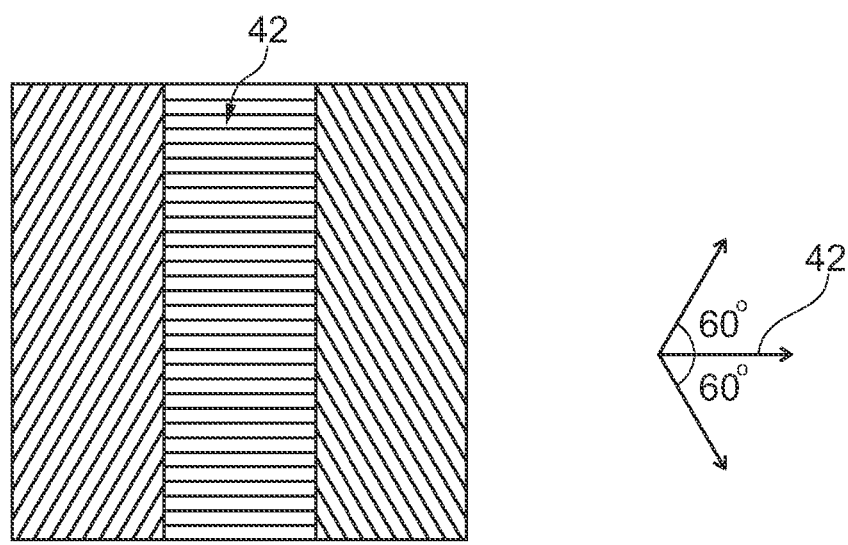
FIGS. 9A and 9B show examples for at least one further coherence direction of the grating arrangement.

According to a further exemplary embodiment, at least twelve line-detector units 40 are provided. A further part of the phase-gratings 52 is provided as further phase-gratings 52 in a further direction and a further part of the analyzer-gratings 68 is provided as further analyzer-gratings 68 in the further direction, each of which is arranged in fixed association with an assigned line of the at least twelve line-detector units 40. For example, a first part of the gratings is provided in an angle of +60° to the scanning direction, a second part of the gratings is provided parallel to the scanning direction and a third part of the gratings is provided in an angle of −60° to the scanning direction. This is illustrated in FIG. 9A showing the arrangement of the directions and not the particular grating layer. As can be seen, a middle portion is provided with a grating structure in the first direction 42, and on both sides a respective angle of 60° is applied to achieve the other two directions, as mentioned above (see also graph with the three directions on the right side of the direction scheme). The line-detector units 40, which are arranged in the radiation direction behind the gratings, are also not shown in FIG. 9A.

Figure 9B:
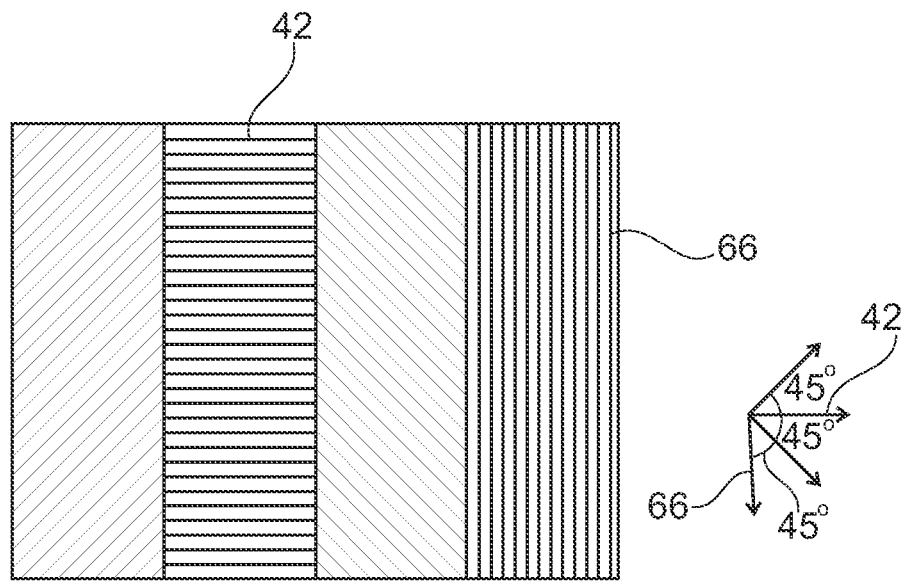

Of course, also more than three directions can be provided for more than three parts. As an example, FIG. 9B shows four directions, wherein the first direction 42 and the second direction 66 are supplemented by two further directions in two different variations of a 45° angle. Thus, a first direction of 0°, a second direction of approximately 45°, a third direction of approximately 90°, and a fourth direction of approximately 135° with respect to the scanning direction is provided (see also graph with the four directions on the right side of the direction scheme). Of course, in such case, at least sixteen line-detector units 40 are provided in order to be able to have at least four lines for each grating orientation, or coherence direction. It is noted that similar to FIG. 9A, also FIG. 9B shows the directions only, and not a particular grating; the line-detector units 40 are also not shown.

Figure 10:
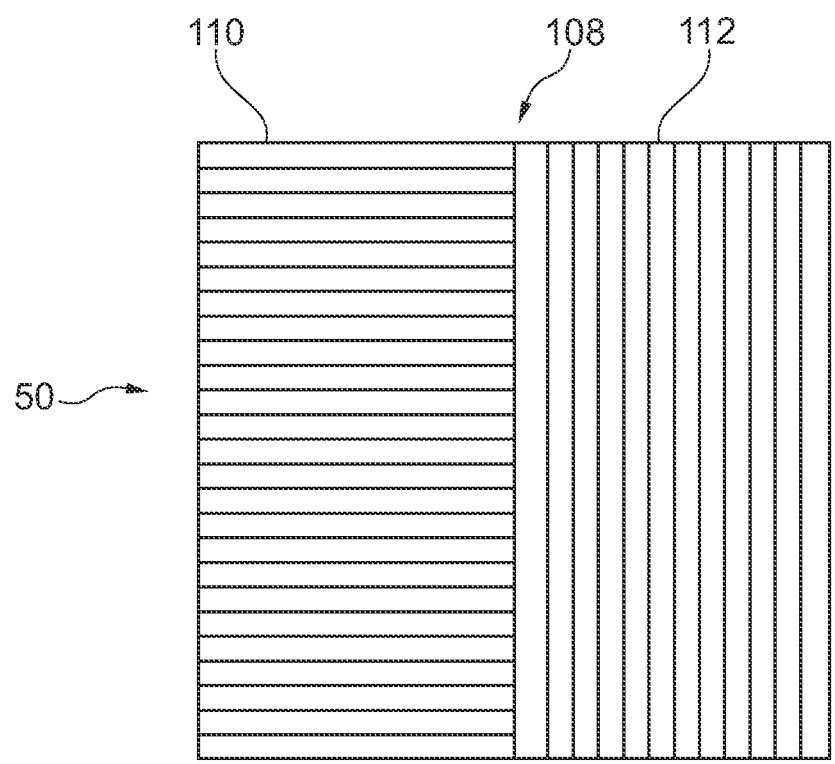
FIG. 10 shows an example for a source-grating according to the present invention.

With respect to FIG. 10, as already indicated above, the source-grating structure 50 is adapted to provide sufficient coherence to the X-ray beam passing the source-grating structure 50 so that after passing the phase-grating structure 46, interference can be observed at the location of the analyzer-grating structure 48. Therefore, the source-grating structure 50 is having a number of linear source-gratings 108, wherein the first part 110 provides coherence with relation to the first direction 22, and wherein at least a second part 112 provides coherence with relation to the second direction 44.

The source-grating structure 50 is provided with a source-grating pitch, wherein the ratio of the source-grating pitch to the analyzer-grating pitch is equal to the ratio of the distance between the source-grating structure 50 and the phase-grating structure 46 to the distance between the phase-grating structure 46 and the analyzer-grating structure 48.

In case of further gratings in a further direction, the further part of the source-grating provides coherence with relation to the further direction (not shown).

Figure 11A:
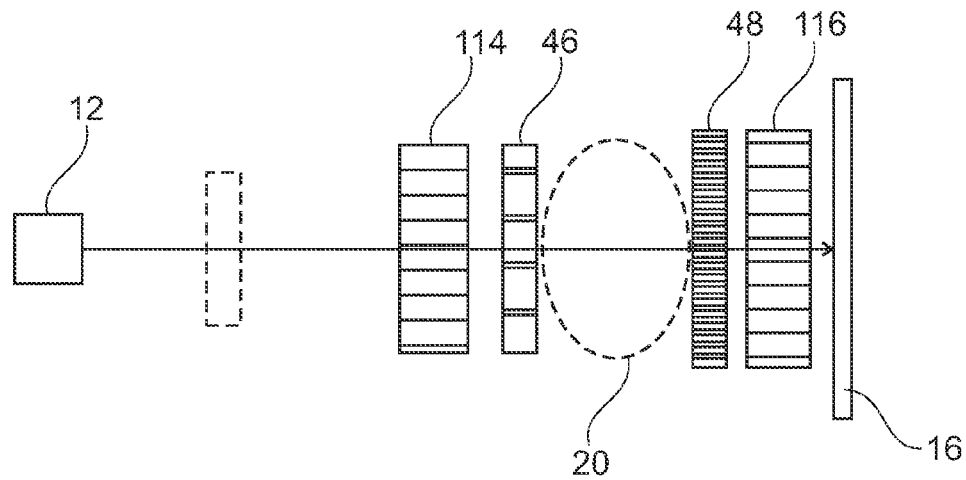
FIGS. 11A and 11B shows an exemplary setup with a pre-collimator and a post-collimator in two different arrangements.
Figure 11B:
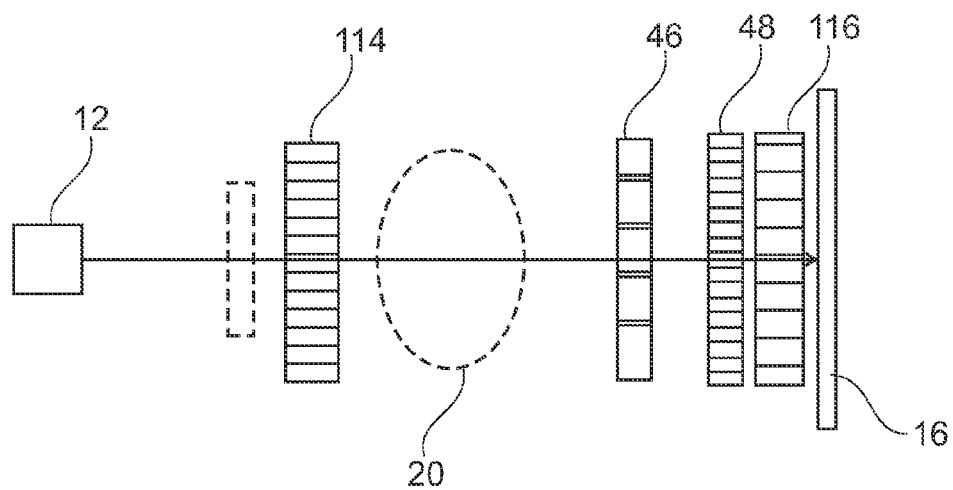

According to the example shown in FIGS. 11A and 11B, a pre-collimator 114 is provided between the X-ray source 12 and the analyzer-grating structure 48 such that an object 20 can be arranged between the X-ray source 12 and the analyzer-grating structure 48. The post-collimator 116 is provided between the analyzer-grating structure 48 and the X-ray detector arrangement 16.

For example, as indicated in FIG. 11A, when starting from the X-ray source 12, the following arrangement is provided: the pre-collimator 114, the phase-grating structure 46, the space to receive an object 20, the analyzer-grating structure 48, the post-collimator 116, and the X-ray detector arrangement 16.

As shown in FIG. 11B, when starting from the X-ray source 12, the following arrangement is provided: the pre-collimator 114, the space to receive the object 20, the phase-grating structure 46, the analyzer-grating structure 48, the post-collimator 116, and the X-ray detector arrangement 16.

The pre-collimator 114 is thus provided between the X-ray source 12 and the phase-grating structure 46 such that an object 20 can be arranged between the X-ray source 12 and the phase-grating structure 46, wherein the post-collimator 116 is provided between the object 20 and the X-ray detector arrangement 16, for example, before or after the analyzer-grating structure 48.

According to a further example, not shown, the phase-grating structure 46 is mounted to the pre-collimator 114, and the analyzer-grating structure 48 is mounted to the post-collimator 116. The object 20 can be arranged between the phase-grating structure 46 and the analyzer-grating structure 48 in a way that the object 20 is arranged closer to the phase-grating structure 46.

The collimators provide the possibility to reduce the X-ray dose applied to the object 20 in such a way that all of the applied dose is used for obtaining image data. Since the line-detector units 40 may be provided in a distance to each other, the collimators can preferably be adapted to the line structure. Thus, only small slices of a patient are radiated at a given time. Due to the movement, the slices can be provided in a sequence such that each point in the region of interest is radiated only once with respect to each grating structure considering the offset, i.e. for example only eight times, each time with a further offset of the analyzer grating structure 48 to the phase grating structure 46, namely four times for one direction 22 and four times for the second direction 44. Of course the sum of eight would be higher in case of one or more further direction(s).

Figure 12A:
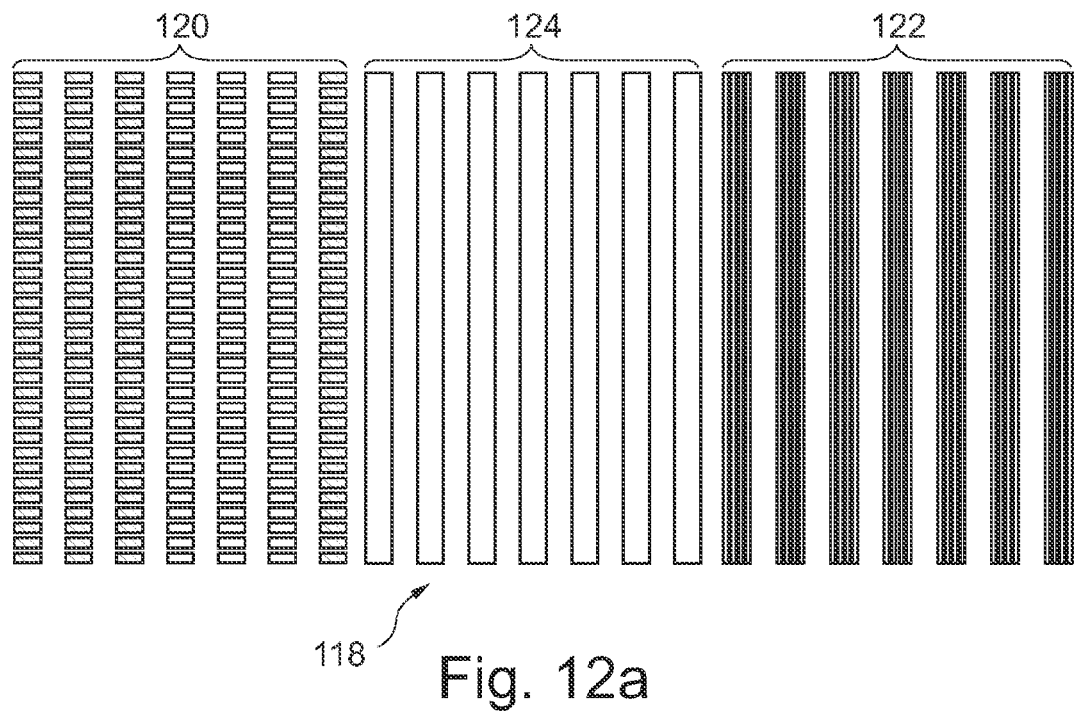
FIGS. 12A and 12B show two different setups for a 21 lines detector arrangement.

According to the present invention, the X-ray imaging system 10 is adapted to acquire at least eight sub-images for phase-retrieval, namely at least four sub-images in relation with one coherence direction, and at least four sub-images for the second coherence direction. For example, as shown in FIG. 12A, the X-ray detector arrangement 16 comprises 21 line-detector units 118, wherein seven adjacent line-detector units 120 are associated with first phase and analyzer-gratings 56, 72 each. Further seven adjacent line-detector units 122 are associated with second phase and analyzer-gratings 62, 78. Still further seven adjacent line-detector units 124 are provided as pure attenuation measuring detector unit. For example, the pure attenuation measuring detector unit 124 is provided between the first and second group of seven lines. However, it must be noted that when providing one or more attenuation detector lines, these can also be provided in a different order, namely the group of the first detector lines followed by the second group relating to the second coherence direction, and then followed by the attenuation line or lines. Further, instead of having seven lines, also another number of lines can be provided as attenuation lines.

Figure 12B:
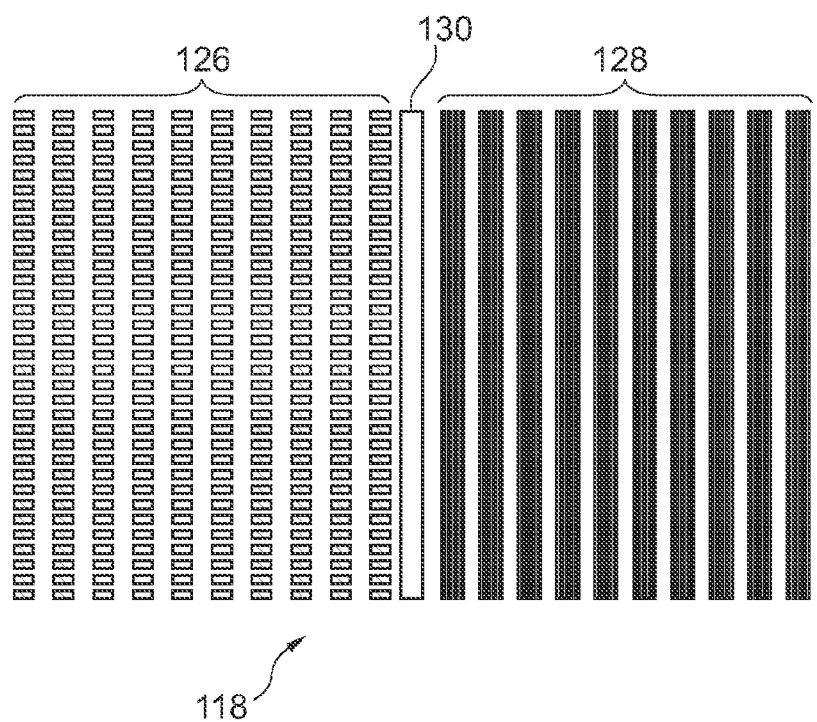

With respect to the source-grating structure 50, according to an example (not shown) the source-grating structure 50 is designed in such a way here that no attenuation takes place by the source-gratings for detector lines that require no coherency at all, for example the central lines in FIGS. 12A and 12B. In other words, the source grating structure 50 may comprise a free section, where no coherence effect to the respective X-ray beam portion is provided for parts of the X-ray beam radiated to pure attenuation measuring detector units 124.

As shown in FIG. 12B, the X-ray detector arrangement 16 comprises 21 line-detector units 118, wherein ten adjacent line-detector units 126 are associated with first phase and analyzer-gratings 56, 72, and further ten adjacent line-detector units 128 are associated with second phase and analyzer-gratings 62, 78. One line-detector unit 130 is provided as a pure attenuation measuring detector unit. For example, the pure attenuation measuring detector unit is provided between the first and the second group of line-detector units.

Figure 13:
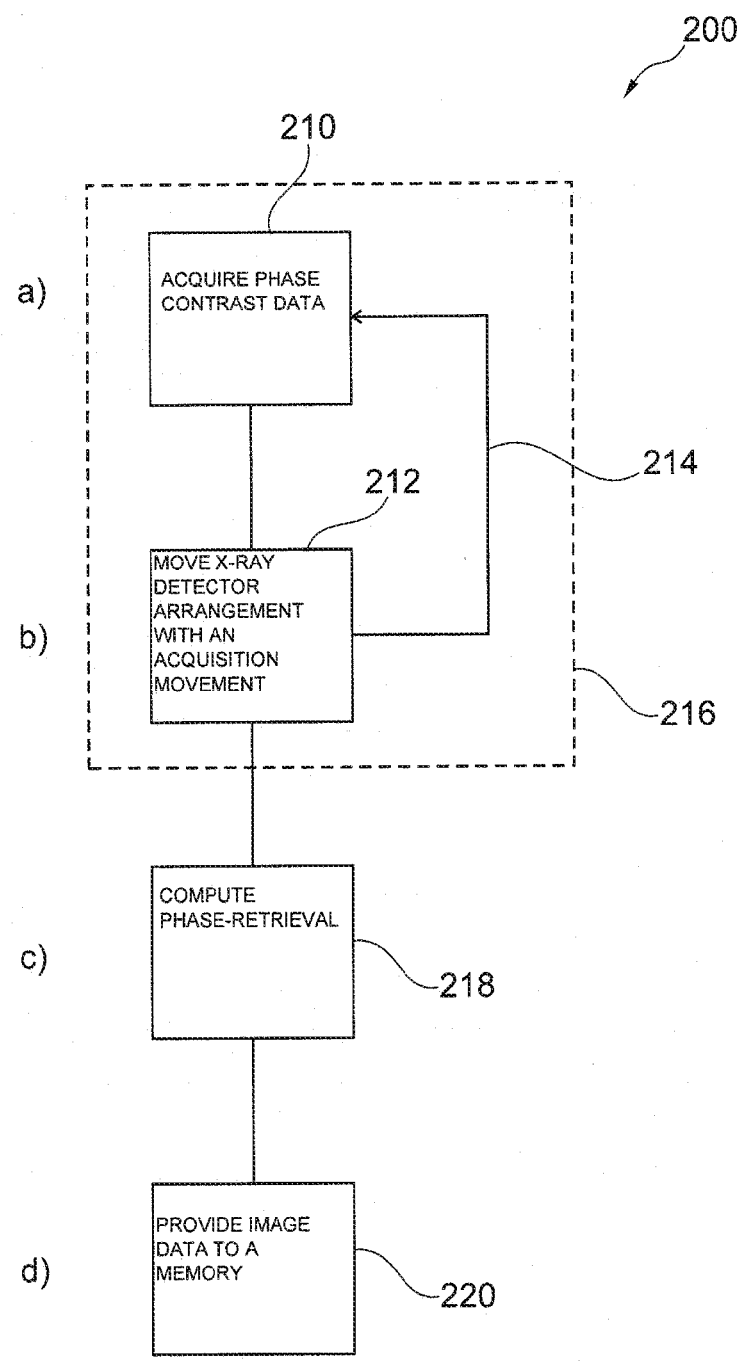
FIG. 13 shows basic steps of a method for X-ray phase contrast imaging of an object according to an exemplary embodiment of the present invention.

FIG. 13 shows a method 200 for X-ray phase contrast imaging of an object 20, comprising the following steps. In a first step 210, phase contrast image sub-data is acquired with an X-ray detector arrangement 16 having at least eight line-detector units 40, wherein at least four line-detector units 40 are relating to a first phase direction of a grating structure, and at least further four line-detector units 40 are relating to a second phase direction. Each line of the line-detector units 40 relating to one phase direction is arranged in fixed association with the grating structure pitch. In a second step 212, the X-ray detector arrangement 16 is moved in relation to the object 20 with an acquisition movement $M_A$ in a single direction. According to the present invention, the first step 210 and the second step 212 are repeatedly performed at least eight times, such that image information of one point is acquired by each of the line-detector units 40. This is indicated with an arrow 214 from the second step 212 back to the first step 210. The provision and repeating of the first and second steps 210 and 212 is also indicated by a surrounding frame 216 in a dotted line. In a third step 218, a phase-retrieval is computed, generating image data for each of the line-detector units 40. In a fourth step 220, the image data is provided for further steps.

The third step may include a gain correction in case different gains on different lines occur.

The first step 210 is also referred to as step a), the second step 212 as step b), the third step 218 as step c), and the fourth step 220 as step d).

According to a further example, not shown, the X-ray source 12, the grating arrangement 18, and the X-ray detector arrangement 16 are mounted to a movement structure 30 that is pivotable around an axis aligned with a focal spot 34 of the X-ray source 12. In the second step 212, the X-ray detector arrangement 16 is pivoted together with the X-ray source 12 in relation to the object 20 for the acquisition movement $M_A$.

The phase-retrieval in step c) provides differential phase data, scatter information, and attenuation data.

In another exemplary embodiment of the present invention, a computer program or a computer program element is provided that is characterized by being adapted to execute the method steps of the method 200 according to one of the preceding embodiments, on an appropriate system.

The computer program element might therefore be stored on a computer unit, which might also be part of an embodiment of the present invention. This computing unit may be adapted to perform or induce a performing of the steps of the method 200 described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method 200 of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method 200 as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the Internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method 200 according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system for phase contrast imaging of an object, comprising:
an X-ray source;
an X-ray detector arrangement; and
a grating arrangement;
wherein the X-ray detector arrangement comprises at least eight line-detector units arranged parallel to each other in a first direction,
wherein the at least eight line-detector units extend linearly in a direction perpendicular to the first direction,
wherein the X-ray source, the X-ray detector arrangement and the grating arrangement are configured to perform an acquisition movement in relation to the object in a scanning direction, the scanning direction being parallel to the first direction,
wherein the grating arrangement comprises a phase-grating structure arranged between the X-ray source and the X-ray detector arrangement, and an analyzer-grating structure arranged between the phase-grating structure and the X-ray detector arrangement,
wherein the phase-grating structure comprises a number of linear phase-gratings, each of which is arranged in a first fixed association with an assigned line-detector unit of the at least eight line-detector units,
wherein a first part of the number of linear phase-gratings comprises first phase-gratings with slits in the first direction, and a second part of the number of linear phase-gratings comprises second phase-gratings with slits in a second direction different than the first direction,
wherein the analyzer-grating structure comprises a number of linear analyzer-gratings, each of which is arranged in a second fixed association with an assigned line-detector unit of the at least eight line-detector units,
wherein a first part of the number of linear analyzer-gratings comprises first analyzer-gratings with slits in the first direction, and a second part of the number of linear analyzer-gratings comprises second analyzer-gratings with slits in the second direction,
wherein at least four adjacent lines of the at least eight line-detector units are associated with the first phase-gratings and the first analyzer-gratings, and wherein at least four adjacent lines of the at least eight line-detector units are associated with the second phase-gratings and the second analyzer-gratings, and
wherein for the acquisition movement, the phase-grating structure and the analyzer-grating structure remain fixed in relation to each other and in relation to the X-ray detector arrangement.

2. The X-ray imaging system according to claim 1, wherein at least one association of the first fixed association and the second fixed association comprises a variation in a phase-grating to an analyzer-grating offset by a fraction 1/n of a pitch of the number of linear analyzer-gratings, wherein n is a number of lines of the at least eight line-detector units associated with one type of phase-grating.

3. The X-ray imaging system according to claim 1,
wherein the at least eight line-detector units comprise at least twelve line-detector units,
wherein a further part of the number of linear phase-gratings comprises further phase-gratings in a further direction and a further part of the number of linear analyzer-gratings comprises further analyzer-gratings in the further direction, each of the further phase-gratings and each of the further analyzer-gratings being arranged in a further fixed association with an assigned line-detector unit of the at least twelve line-detector units, and wherein the further direction is different from the first and second directions.

4. The X-ray imaging system according to claim 1, further comprising a movement structure, wherein for the acquisition movement, the X-ray source, the grating arrangement and the X-ray detector arrangement are mounted to the movement structure that is configured to be pivotable around an axis aligned with a focal spot of the X-ray source.

5. The X-ray imaging system according to claim 1, wherein the X-ray imaging system is configured to acquire at least eight sub-images for phase-retrieval.

6. The X-ray imaging system according to claim 1, wherein the at least eight line-detector units comprise at least one further line-detector unit configured as a pure attenuation measuring detector without any associated phase-grating structure and analyzer-grating structure.

7. The X-ray imaging system according to claim 1,
wherein the grating arrangement comprises a source-grating structure arranged between the X-ray source and the phase-grating structure,
wherein the source-grating structure is configured to provide sufficient coherence to an X-ray beam passing the source-grating structure, so that after passing the phase-grating structure, interference can be observed at a location of the analyzer-grating structure, and
wherein the source-grating structure comprises a number of linear source-gratings,
wherein a first part of the number of linear source-gratings provides coherence with relation to the first direction, and
wherein at least a second part of the number of linear source-gratings provides coherence with relation to the second direction.

8. The X-ray imaging system according to claim 7, wherein the at least eight line-detector units comprise at least one further line-detector unit configured as a pure attenuation measuring detector without any associated phase-grating structure and analyzer-grating structure, and
wherein the source-grating structure further comprises a free section, where no coherence effect to a respective X-ray beam portion is provided for parts of the X-ray beam radiated to the pure attenuation measuring detector.

9. The X-ray imaging system according to claim 1, further comprising:
a pre-collimator provided between the X-ray source and the analyzer-grating structure such that the object can be arranged between the X-ray source and the analyzer-grating structure; and
a post-collimator provided between the analyzer-grating structure and the X-ray detector arrangement.

10. A method for X-ray phase contrast imaging of an object, comprising acts of:
acquiring phase contrast image sub-data with an X-ray detector arrangement having at least eight line-detector units,
wherein at least four line-detector units of the at least eight line-detector units are relating to a first phase direction of a grating structure and at least a further four line-detector units of the at least eight line-detector units are relating to a second phase direction, and
wherein each line-detector unit of the at least eight line-detector units relating to one phase direction of one of the first phase direction and second phase direction is arranged in a fixed association with a grating structure pitch;
moving the X-ray detector arrangement in relation to the object with an acquisition movement in a single direction,
wherein the X-ray detector arrangement and an X-ray source are mounted to a movement structure that is configured to be pivotable around an axis aligned with a focal spot of the X-ray source,
wherein, in the moving act, the X-ray detector arrangement is pivoted together with the X-ray source in relation to the object, and
wherein the acquiring act and the moving act are repeatedly performed at least eight times such that image information of one point is acquired by each of the at least eight line-detector units;
computing a phase-retrieval for generating image data for each of the at least eight line-detector units; and
providing the image data to a memory for storage.

11. The method according to claim 10, wherein the act of computing the phase-retrieval for generating the image data for each of the at least eight line-detector units comprises providing:
differential phase data;
scatter information; and
attenuation data.

12. A non-transitory computer readable medium comprising computer instructions for X-ray phase contrast imaging of an object which, when executed by a processor, configure the processor to perform acts of:
acquiring phase contrast image sub-data with an X-ray detector arrangement having at least eight line-detector units,
wherein at least four line-detector units of the at least eight line-detector units are relating to a first phase direction of a grating structure and at least a further four line-detector units of the at least eight line-detector units are relating to a second phase direction, and
wherein each line-detector unit of the at least eight line-detector units relating to one phase direction of one of the first phase direction and second phase direction is arranged in a fixed association with a grating structure pitch;
moving the X-ray detector arrangement in relation to the object with an acquisition movement in a single direction,
wherein the X-ray detector arrangement and an X-ray source are mounted to a movement structure that is configured to be pivotable around an axis aligned with a focal spot of the X-ray source,
wherein, in the moving act, the X-ray detector arrangement is pivoted together with the X-ray source in relation to the object, and
wherein the acquiring act and the moving act are repeatedly performed at least eight times such that image information of one point is acquired by each of the at least eight line-detector units;
computing a phase-retrieval for generating image data for each of the at least eight line-detector units; and
storing the image data to a memory.

* * * * *